United States Patent [19]

Matzinger et al.

[11] Patent Number: 5,515,170
[45] Date of Patent: May 7, 1996

[54] ANALYTE DETECTION DEVICE HAVING A SERPENTINE PASSAGEWAY FOR INDICATOR STRIPS

[75] Inventors: David P. Matzinger, Menlo Park; George M. Daffern, Sunnyvale, both of Calif.

[73] Assignee: LifeScan, Inc., Mountain View, Calif.

[21] Appl. No.: 302,282

[22] Filed: Sep. 8, 1994

[51] Int. Cl.[6] .......................... G01J 3/52; G01N 21/47; G01N 21/00
[52] U.S. Cl. .................. 356/423; 356/446; 356/244; 422/82.05; 422/58
[58] Field of Search .................. 422/56, 58, 82.05, 422/82.09; 250/561; 356/244, 446, 423

[56] References Cited

U.S. PATENT DOCUMENTS

| | | | |
|---|---|---|---|
| 3,552,928 | 1/1971 | Fetter | 422/56 |
| 3,980,437 | 9/1976 | Kishimoto et al. | 356/445 |
| 3,992,158 | 11/1976 | Przybylowicz et al. | 422/58 |
| 4,042,335 | 8/1977 | Clement | 422/56 |
| 4,125,372 | 11/1978 | Kawai et al. | 422/56 |
| 4,144,306 | 3/1979 | Figueras | 422/56 |
| 4,255,384 | 3/1981 | Kitajima et al. | 422/56 |
| 4,258,001 | 3/1981 | Pierce et al. | 422/56 |
| 4,292,272 | 9/1981 | Kitajima et al. | 422/56 |
| 4,452,887 | 6/1984 | Kitajima et al. | 422/56 |
| 4,509,859 | 4/1985 | Markart et al. | 356/446 |
| 4,592,893 | 6/1986 | Poppe et al. | 422/56 |
| 4,682,895 | 7/1987 | Costello | 356/402 |
| 4,714,874 | 12/1987 | Morris et al. | 422/58 |
| 4,774,192 | 9/1988 | Terminiello et al. | 422/56 |
| 4,780,283 | 10/1988 | Meinecke et al. | 422/82.05 |
| 4,790,979 | 12/1988 | Terminiello et al. | 422/56 |
| 4,816,224 | 3/1989 | Vogel et al. | 422/56 |
| 4,937,050 | 6/1990 | Meinecke et al. | 356/244 |
| 4,978,503 | 12/1990 | Shanks et al. | 356/244 |
| 4,984,895 | 1/1991 | Kobayashi et al. | 356/423 |
| 4,994,238 | 2/1991 | Daffern et al. | 422/56 |
| 5,029,583 | 7/1991 | Meserol et al. | 128/633 |
| 5,037,614 | 8/1991 | Makita et al. | 422/82.05 |
| 5,059,394 | 10/1991 | Phillips et al. | 422/82.05 |
| 5,082,516 | 1/1992 | Akao et al. | 422/56 |
| 5,095,025 | 3/1992 | Tanaka et al. | |
| 5,095,026 | 3/1992 | Schoenwald et al. | |
| 5,120,507 | 6/1992 | Sano et al. | 422/82.05 |
| 5,167,145 | 12/1992 | Butler et al. | 356/39 |
| 5,174,963 | 12/1992 | Fuller et al. | 356/446 |
| 5,192,502 | 3/1993 | Attridge et al. | 356/246 |
| 5,211,914 | 5/1993 | Vogel et al. | 422/56 |
| 5,232,668 | 8/1993 | Grant et al. | 422/82.05 |
| 5,236,940 | 8/1993 | Audjau et al. | |
| 5,246,858 | 9/1993 | Arbuckle et al. | 356/446 |
| 5,252,293 | 10/1993 | Drbal et al. | 422/56 |
| 5,277,870 | 1/1994 | Fuller et al. | 356/446 |
| 5,306,623 | 4/1994 | Kiser et al. | 435/14 |

FOREIGN PATENT DOCUMENTS

| | | |
|---|---|---|
| 0333099 | 9/1989 | European Pat. Off. ............... 356/423 |
| 4035052A1 | 11/1989 | Germany . |
| 4-113268 | 4/1992 | Japan . |
| 938029 | 8/1961 | United Kingdom . |

OTHER PUBLICATIONS

"Azo Dyes by Oxidative Coupling, VIII*", S. Hunig and Kobrich, Liebigs Ann. Chem. 617, 216 (1958).
"New Contributions to the Optics of Intensely Light-Scattering Materials, Part I"; Journal of Optical Society of America, vol. 38, No. 5, May 1948, pp. 448-457.

Primary Examiner—Frank Gonzalez
Assistant Examiner—Jason D. Eisenberg
Attorney, Agent, or Firm—James Riesenfeld

[57] ABSTRACT

An apparatus comprising a passageway for accepting a strip for determining the presence or quantity of an analyte is provided. The passageway has a serpentine shape to maintain the strip against an optical aperture in the passageway wall, insuring that a constant optical reading is obtained.

6 Claims, 6 Drawing Sheets

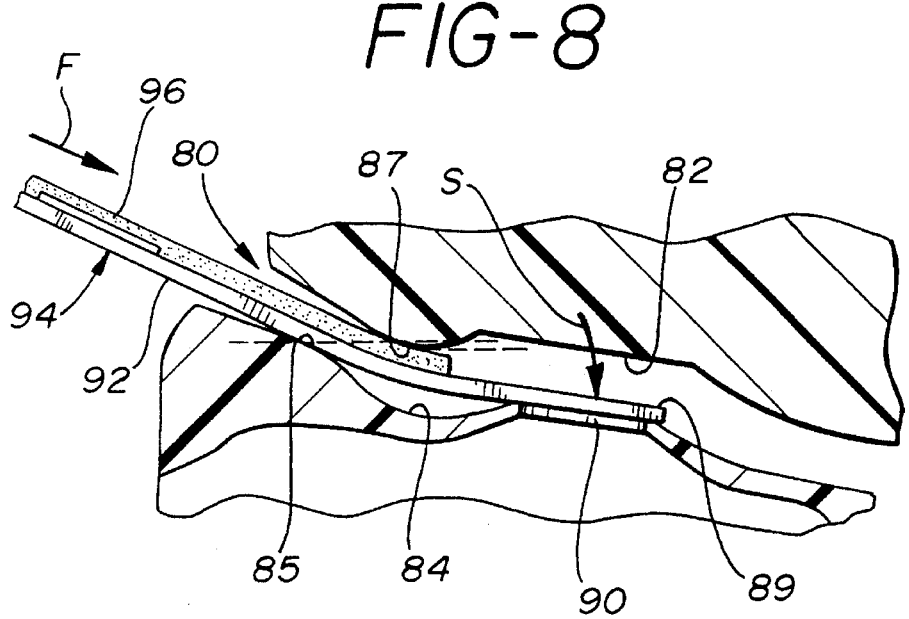
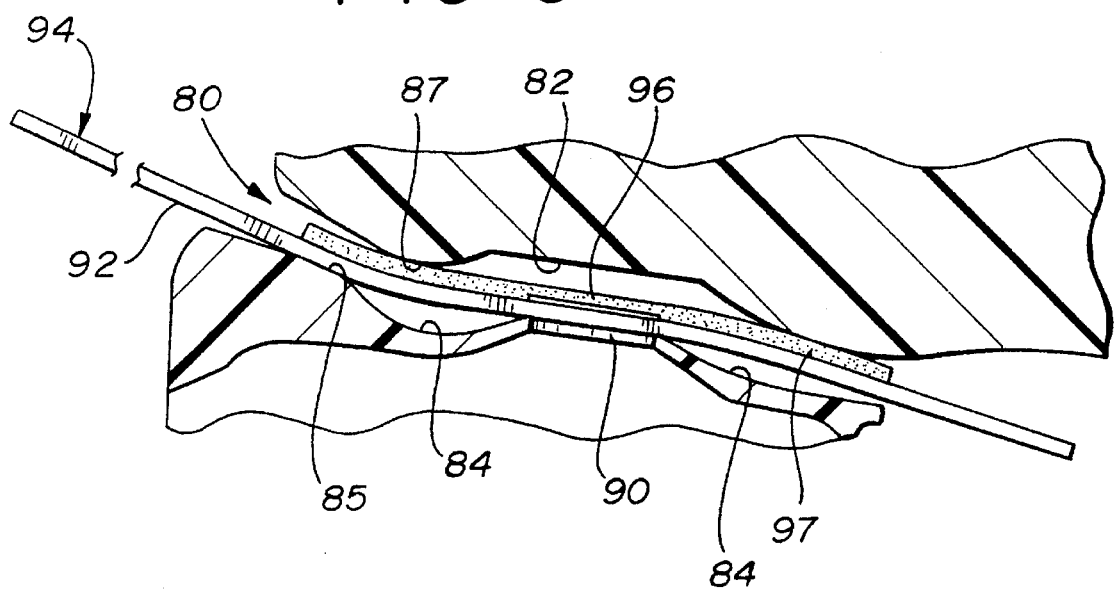

ANALYTE DETECTION DEVICE HAVING A SERPENTINE PASSAGEWAY FOR INDICATOR STRIPS

FIELD OF THE INVENTION

The present invention relates to a test device and method for the optical determination of analytes in aqueous fluids, particularly whole blood. In one preferred embodiment it concerns a test device and method for optically measuring the concentration of glucose in whole blood.

BACKGROUND OF THE INVENTION

The quantification of chemical and biochemical components in colored aqueous fluids, in particular colored biological fluids such as whole blood and urine and biological fluid derivatives such as blood serum and blood plasma, is of ever-increasing importance. Important applications exist in medical diagnosis and treatment and in the quantification of exposure to therapeutic drugs, intoxicants, hazardous chemicals and the like. In some instances, the amounts of materials being determined are either so minuscule—in the range of a microgram or less per deciliter—or so difficult to precisely determine that the apparatus employed is complicated and useful only to skilled laboratory personnel. In this case the results are generally not available for some hours or days after sampling. In other instances, there is often an emphasis on the ability of lay operators to perform the test routinely, quickly and reproducibly outside a laboratory setting with rapid or immediate information display.

One common medical test is the measurement of blood glucose levels by diabetics. Current teaching counsels diabetic patients to measure their blood glucose level from two to seven times a day depending on the nature and severity of their individual cases. Based on the observed pattern in the measured glucose levels, the patient and physician together make adjustments in diet, exercise and insulin intake to better manage the disease. Clearly, this information should be available to the patient immediately.

Currently a method widely used in the United States employs a test article of the type described in U.S. Pat. No. 3,298,789 issued Jan. 17, 1967 to Mast. In this method a sample of fresh, whole blood (typically 20–40 µl) is placed on an ethylcellulose-coated reagent pad containing an enzyme system having glucose oxidase and peroxidase activity. The enzyme system reacts with glucose and releases hydrogen peroxide. The pad also contains an indicator which reacts with the hydrogen peroxide in the presence of peroxidase to give a color proportional in intensity to the sample's glucose level.

Another popular blood glucose test method employs similar chemistry but uses, in place of the ethylcellulose-coated pad, a water-resistant film through which the enzymes and indicator are dispersed. This type of system is disclosed in U.S. Pat. No. 3,630,957 issued Dec. 28, 1971 to Rey et al.

In both cases the sample is allowed to remain in contact with the reagent pad for a specified time (typically one minute). Then, in the first case, the blood sample is washed off with a stream of water while in the second case, it is wiped off the film. The reagent pad or film is then blotted dry and evaluated. The evaluation of the analyte concentration is made either by comparing color generated with a color chart or by placing the pad or film in a diffuse reflectance instrument to read a color intensity value.

While the above methods have been used in glucose monitoring for years, they do have certain limitations. The sample size required is rather large for a finger stick test and is difficult to achieve for some people whose capillary blood does not express readily.

In addition, these methods share a limitation with other simple lay-operator colorimetric determinations in that their result is based on an absolute color reading which is in turn related to the absolute extent of reaction between the sample and the test reagents. The fact that the sample must be washed, blotted or wiped off the reagent pad after the timed reaction interval requires that the user be ready at the end of the timed interval and wipe or apply a wash stream at the required time. The fact that the reaction is stopped by removing the sample leads to some uncertainty in the result, especially in the hands of the home user. Overwashing, overblotting or overwiping can give low results and underwashing can give high results.

Another problem that often exists in simple lay-operator determinations is the necessity for initiating a timing sequence when blood is applied to a reagent pad. A user will typically have pricked his or her finger to obtain a blood sample and will then be required to simultaneously apply the blood from the finger to a reagent pad while starting a timer with his or her other hand, thereby requiring the use of both hands simultaneously. This is particularly difficult since it is often necessary to ensure that the timer is started only when blood is applied to the reagent pad. All of the prior art methods require additional manipulations or additional circuitry to achieve this result. Accordingly, simplification of this aspect of reflectance reading instruments is desirable.

Great improvements have been achieved upon the introduction of the systems described in U.S. Pat. Nos. 5,179,005, 5,059,394, 5,049,487, and 4,935,346 wherein an apparatus is provided for accepting a test strip having a test pad, one surface of which comprises a reaction zone adapted to be optically readable by said apparatus. The test strip is inserted into the apparatus, the apparatus is started and then whole blood is applied onto the test pad. At least a portion of such blood is allowed to permeate to the reaction zone whereby any analyte present therein will react with color-producing reagents in the test pad to alter the light reflectance characteristics of the reaction zone. The reflectance of the reaction zone is then a measure of the presence and/or quantity of analyte present in the blood sample. As described in the aforementioned patents, this system does not require a large sample of blood nor does it require the user to undertake timed manipulations with respect to the beginning or end of the reaction. Instead, because the strip is first inserted into the apparatus prior to the application of the sample, a standard reflectance reading of the reaction zone in the dry state may be obtained. The beginning of the reaction can be detected by the first "breakthrough" of the liquid sample onto the reaction zone by monitoring the reflectance and comparing the reading to the standard reflectance of the dry reaction zone. A reflectance reading taken at a predetermined time after the reaction has begun when compared to the standard reflectance, i.e., the dry reaction zone reading, will be indicative of the quantity of analyte present in the sample.

While the above described system does indeed solve the problems of the prior art and relieves the user of the burden of measurement and timing, it does require that the user apply a sample of blood onto the strip while the strip is in the apparatus. For the most part this represents no problem to the vast majority of users. However, certain users suffer from handicaps such as poor vision or impaired motor coordination so that the accurate application of blood from such users' pricked fingers to the strip in place on the apparatus, represents a hardship. Further, for institutional users, for example, there is the possibility that some quantity of blood remains on the device from a prior user, since the systems necessitate applying one's pricked finger to the device. In such instances there is the need to disinfect the device between users.

Accordingly, for the above reasons, in the case of at least some users, it would be preferable to first apply the blood sample to the strip prior to inserting the strip into the apparatus. Unfortunately, by doing so the apparatus no longer has the capability of reading reflectance of the dry, unreacted, reaction zone, i.e., at no time is the dry reaction zone presented to the apparatus. This reading was necessary in the prior devices to provide a calibration standard for determining the reflectance change as a result of the reaction and hence the presence and/or quantity of the analyte in the sample.

In copending, commonly assigned U.S. Ser. No. 08/302, 160, filed Sep. 8, 1994, entitled "Optically Readable Strip For Analyte Detection Having On-Strip Standard", incorporated herein by reference, there is described a strip, apparatus, and methodology for allowing the user to apply a sample to the strip before inserting it into the reading apparatus while also providing a calibrated standard. This above-referenced patent application teaches a strip which comprises a portion for having the liquid applied thereto, this portion having an optically visible surface (i.e., at least with respect to the optics of the apparatus to be employed with the strip) defining a reaction zone. The reaction zone is such that its reflectance varies as a function of the quantity of analyte present in the applied liquid. Preferably, such is accomplished by the analyte reacting with reactants to produce a color change of the reaction zone. The test strip further comprises a standard zone of contrasting reflectance, relative to the reflectance of the reaction zone. The standard zone is positioned on the strip so as to lead the reaction zone as the strip is inserted into the apparatus.

Accordingly, the apparatus may be provided with optical means for sequentially determining the reflectance value of the standard zone as the strip is being inserted into its fully inserted position in the apparatus and the reflectance value of the reaction zone after the strip has been inserted. Additionally, the apparatus is provided with means for calculating the presence and/or quantity of the analyte in question as a function of the standard zone reflectance and the reaction zone reflectance.

Owing to the configuration of the strip, and specifically, the provision of a standard zone leading the reaction zone, the aforementioned apparatus need be provided with only one set of optics, e.g., one light emitting diode and one light detector for reading the reflection at a single position along the path of the strip.

In operation, the user turns on the apparatus, applies the sample to a fresh strip and then inserts the strip fully into the apparatus and reads the results. Without intervention of the user, the strip, configured as described, allows the apparatus to read the reflectance of light incident upon standard zone as it passes the optics of the apparatus as the strip is inserted. This reading is then calibrated to account for variations owing to changes in the apparatus from the factory condition and to lot-to-lot variations in the strip. The fully inserted strip thereafter presents the reaction zone to the optics of the apparatus and the reflectance of this surface may be read. Means are provided for the apparatus to calculate and report the analyte presence or concentration as a function of these readings.

The above-described system has gone a long way toward easing the user's task in determining analyte concentration. It will be appreciated, however, that it is fundamental to the successful optical reading of a strip on which liquid has been applied, that the strip is inserted into the apparatus in a precise relationship with respect to the optics of the apparatus. It will be appreciated that when attempting to determine the presence of an analyte (and more importantly, when attempting to determine the quantity of an analyte) in a sample using optical techniques, consistent, precise presentation of the surface to be optically read must be adhered to. Absent such consistency, anomalous results will be reported by the highly sensitive instruments employed.

This need for a device insuring precision is difficult to satisfy in prior devices and hence the art has gone to substantial design efforts in attempting to provide it. Thus, for example, in U.S. Pat. No. 5,120,507, to Sano, a spring loaded plate is provided in a device for reading a strip. The spring loaded plate bears against the strip and holds it flat to the optical viewing means. Such a system aids in the precision of presenting the surface to be read to the optics, but falls short of solving the problem.

The precision problem is far more difficult to solve in the case of the system described in the aforementioned and referenced U.S. patent application Ser. No. 08/302,160 wherein not only is the reaction zone to be read by the optics but likewise, the leading portion of the strip is to be optically read and used as a calibrated standard zone for determining the analyte quantity. In such a system, rather than one area being read by the optics, a longitudinally extending leading portion of the strip is to be read as well. Moreover, this portion is to be read "on the fly" as the strip is being inserted. Further still, as described in the aforementioned patent application, the standard zone is essentially an area on a thin strip support which carries a relatively thick test pad having an exposed surface which, in turn, is to be read as the reaction zone. Accordingly, the strip varies in thickness along its longitudinal axis. Optical readings must be taken along this axis as the strip passes the optics during insertion and after having been fully inserted and, hence, the areas to be read must be precisely presented to the optics, the varying thickness notwithstanding. In the aforementioned patent application, a resilient ring like biasing means is described which has the property of providing biasing pressure against the strip when viewable to the optics of the apparatus irrespective of the varying thickness of the strip as it is being inserted. While such a method works, it is relatively expensive to incorporate into the device and, accordingly, alternatives have been sought.

SUMMARY OF THE INVENTION

In accordance with the teachings of this invention, a system is provided whereby a strip can be inserted into an optically reading apparatus with great assurance that the surface or surfaces to be read will be presented to the optics in a uniform manner. Moreover, the teachings of this invention are directed towards accomplishing this without resort to complex or expensive designs or mechanisms.

Specifically, this invention is directed towards an apparatus for determining the presence or quantity of analyte in a sample applied to a portion of a longitudinally extending test strip to be inserted into the apparatus and having an insertion end and a trailing end. A portion of the test strip is provided with an optically visible surface (with respect to the optics of the apparatus) defining a reaction zone which varies in its ability to reflect light as a function of the quantity of analyte present in the applied sample.

The apparatus is provided with a strip passageway into which the strip is to be inserted, the passageway being defined as lying between first and second walls. These walls extend longitudinally from an upstream open end of the passageway, for inserting the leading edge of the test strip into the apparatus, to a downstream opposed end of the passageway. It is contemplated that a portion of the strip, when inserted in the passageway, is to be read by optics (e.g., an LED/reflected light detector combination) housed within the apparatus. Accordingly, the passageway is also provided with an optical aperture in the first wall of the passageway for rendering such portion of the inserted strip optically visible therethrough to these optics.

In accordance with the teachings herein, the walls forming the passageway are of a particular shape so as to insure precise presentation of the strip to the aperture and, hence, to the optics. Specifically, the first wall is provided with a first strip bearing surface and the second wall is provided with a second strip bearing surface downstream from the first strip bearing surface with both such strip bearing surfaces being located upstream of the aperture. The two bearing surfaces are further oriented with respect to each other so that a portion of the strip to be read by the optics is urged against the aperture when such portion overlies the aperture. Generally, this is accomplished by providing the bearing surfaces oriented to force the strip into a curved shape concave, to the second wall, and by providing a strip having spring-like properties. The spring-like strip, forced into such curved shape will be biased to straighten and hence be urged against the aperture. To accomplish this curvature, the two bearing surfaces should be oriented so that the upstream first bearing surface is no lower than one strip thickness below the downstream second bearing surface when the strip is between the bearing surfaces and positioned to be read by the optics. The term "higher" or "lower" is used herein in the sense of the normal distance above (or below) the plane of the aperture. It will also be appreciated that the strip may have different thicknesses along its length and that it is desirable to read the strip at various portions along its length. Accordingly, the orientation of the two bearing surfaces should be such that at all positions the above prescribed relationships hold true, i.e., the upstream first bearing surface is no more than a strip thickness lower than the downstream second bearing surface when the downstream portion of the strip is in a desired reading position over the aperture.

In a preferred embodiment, the second wall is provided with a third bearing surface positioned downstream of the aperture. Preferably, this third bearing surface is oriented no higher than one strip thickness above the plane of the aperture. Accordingly, the leading portion of the strip, having reached a position downstream of the aperture, will bear against this third bearing surface and deflect into a curved shaped concave to the first wall. This deflection will maintain the portion of the strip overlying the aperture firmly against the aperture.

BRIEF DESCRIPTION OF THE DRAWINGS

The present invention can be more readily understood by reference to the following detailed description when read in conjunction with the attached drawings wherein:

FIG. 8 is a schematic, fragmented, longitudinal cross-sectional view of a passageway embodying the teachings of this invention, with a strip being inserted therein; and FIG. 9 is a schematic, fragmented, longitudinal cross-sectional view of a passageway embodying further teachings of this invention with a strip fully inserted.

DETAILED DESCRIPTION OF THE INVENTION

Figure 1:
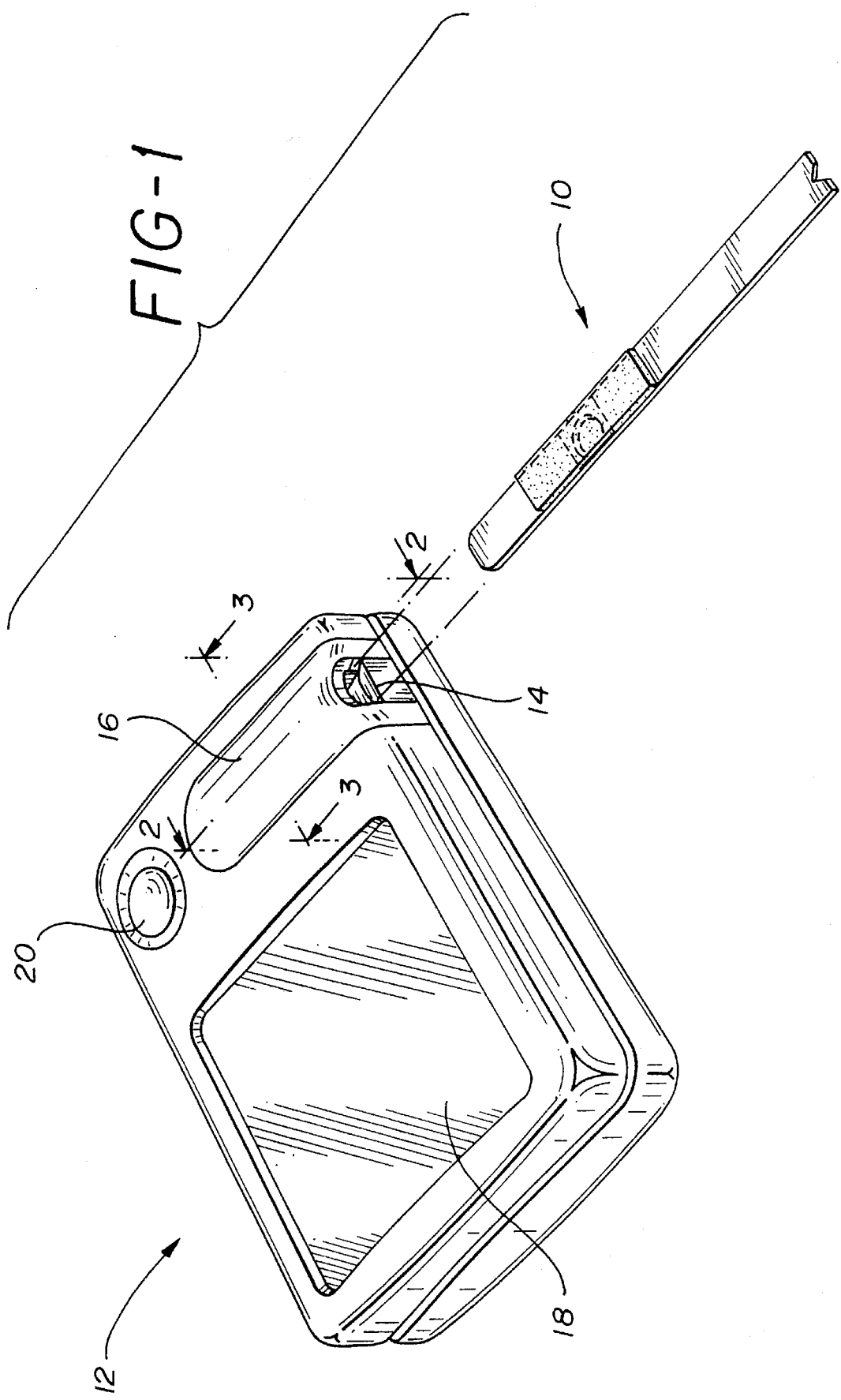
FIG. 1 is an exploded, perspective view of a strip and apparatus embodying the teachings of this invention.

Turning now to the drawings, FIG. 1 illustrates in exploded, perspective view, a strip 10 for applying a sample thereon and for inserting such sample laden strip 10 into an optical reading apparatus 12. Embodiments of the strip 10 and apparatus 12 will generally be described hereinafter in terms of detection and quantification of glucose but it will be understood by those skilled in the art that the teachings herein are not limited to glucose determinations, but instead may be applied to other analyte determinations. Further, for the purpose of simplification and clarity, the strip 10, the apparatus 12 and their respective component parts shall all be described as being in the orientation shown in the drawings and terms such as "the bottom" and "the top" shall be employed consistent with such orientation. It will be appreciated, however, that this method of description is merely convenient and that in no way is the invention restricted to such orientation and, in fact, the strip and strip holder may be rotated through any angle relative to the apparatus and the teachings herein still apply.

Figure 2:
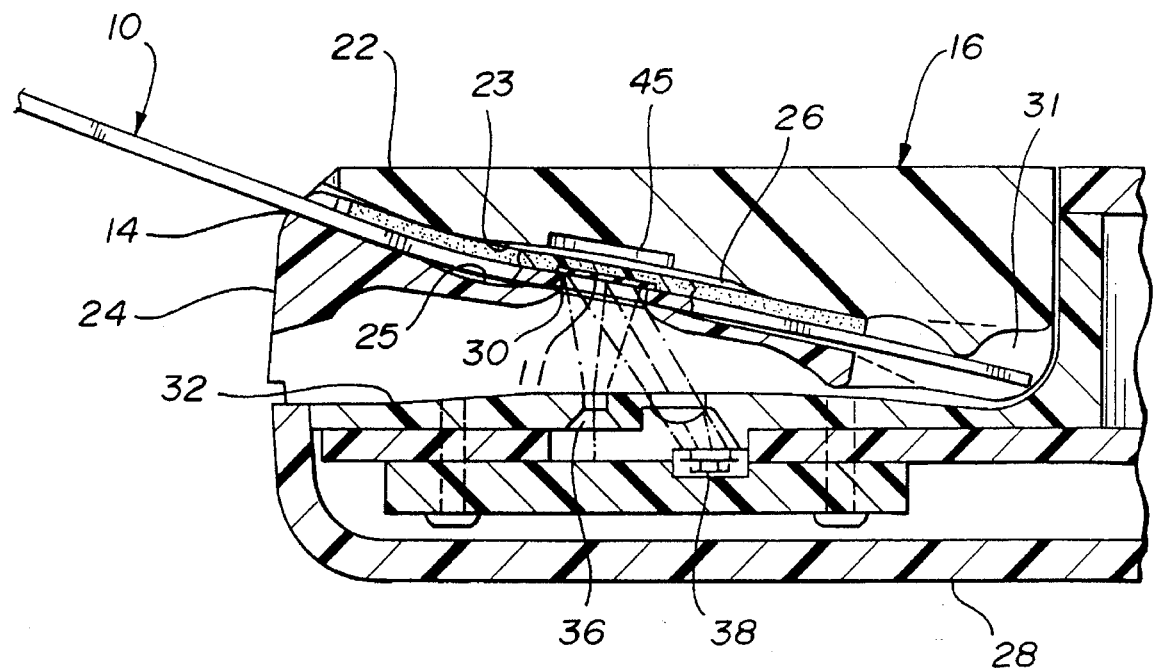
FIG. 2 is a partial, longitudinal, cross-sectional view taken along line 2—2 of FIG. 1 and illustrating the strip fully inserted into the apparatus.
Figure 3:
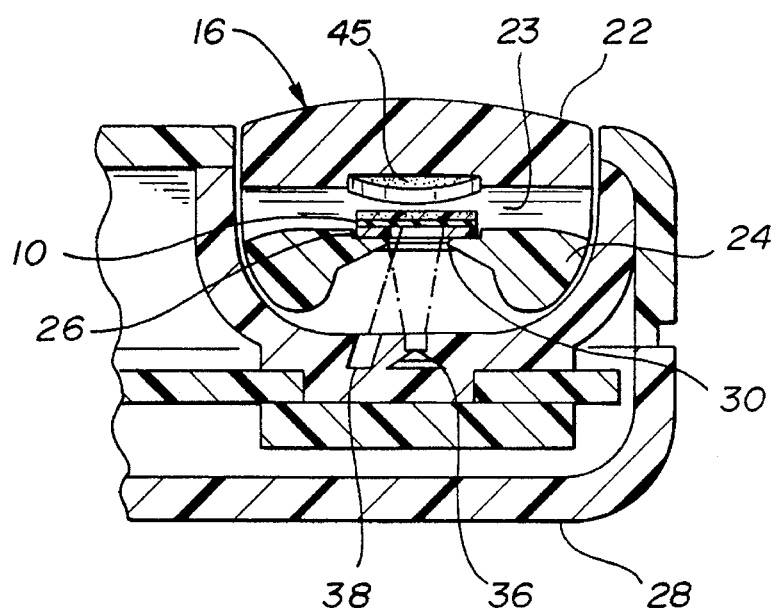
FIG. 3 is a partial, transverse, cross-sectional view, taken along line 3—3 of FIG. 1 and illustrating the strip fully inserted into the apparatus.

As can be see in FIG. 1, the strip 10 is adapted to be inserted longitudinally, into an open end 14 of a strip holder 16 carried on apparatus 12. Strip holder 16, shown in more detail in FIGS. 2 and 3, is preferably removable from apparatus 12 for cleaning. The apparatus 12 is provided on its visible surface with a screen 18 on which messages, instructions, error warnings, and most importantly, results may be displayed by means such as liquid crystal displays as are well known in the art. Such information may be conveyed by letters, words, numbers or icons. Additionally, apparatus 12 is provided with a power switch for activating the apparatus, preferably with batteries and such power switch is shown as push button 20 on the drawings.

Referring now to FIGS. 2 and 3, illustrated therein in longitudinal and transverse cross-sectional views respectively, is the removable strip holder 16 with a strip 10 fully inserted therein, together with fragmentary views of the adjacent parts of the apparatus 12. The strip holder 16 is comprised of a lower guide 24 having a passageway wall 25 and a upper guide 22 having passageway wall 23 which together define a channel or strip passageway 26 into which the strip is inserted via open end 14. Passageway 26 terminates at opposed end 31. It should be noted that the passageway 26 is canted at an angle with respect to the plane of the bottom 28 of the apparatus 12, so as to facilitate the insertion of strip 10 into the apparatus when the apparatus is sitting on a flat surface.

The lower guide 24 is provided with an aperture 30 through wall 25 through which the bottom surface 11 of the strip can be "seen" by the optics located below lower guide 24. As will be understood hereinafter, the aperture 30 is positioned at a point through wall 25 so as to "see" the bottom surface of a reaction zone of strip 10 when the strip 10 is fully inserted into passageway 26.

The optics for the apparatus are located in optic block 32 affixed to apparatus 12. Optic block 32 contains a light emitting diode (LED) 36 capable of directing light through aperture 30, upon a surface such as the lower surface of the strip. The light emitting diode is preferably one which emits light of essentially a uniform wavelength in rapid bursts, hereinafter referred to as "chops" for a period of time, each time it is activated. For the purposes of glucose determination, it has been found preferable to employ two such LED's, each emitting light at a different wavelength and preferably at 660 and 940 nanometers (LED 660 and LED 940, respectively). The optic block 32 also comprises a photodetector 38, a device capable of intercepting light reflected from the surface upon which the LED's focus and converting such light into a measurable voltage.

Incorporated into wall 23 and aligned with aperture 30 is a colored target, preferably gray, hereinafter referred to as the "gray target" 45. The gray target 45 presents to the optics a surface for assuring the correct calibration of the apparatus before the strip is inserted.

As will be described in greater detail herein, means are provided to assure that when surfaces of the strip 10 are presented to the optics through aperture 30, these surfaces are so presented in a precise manner. Such means comprise providing walls 23 and 25 with a specific configuration such that, in the preferred embodiment, the passageway 26 has an S-serpentine configuration. It will be understood by consideration of the drawings and the description therein, that such serpentine shape is only a moderate, but highly effective, variance from a straight walled passageway and when viewed in FIGS. 2 and 3, is noticeable only upon close scrutinization. This point will be expanded upon herein.

Figure 4:
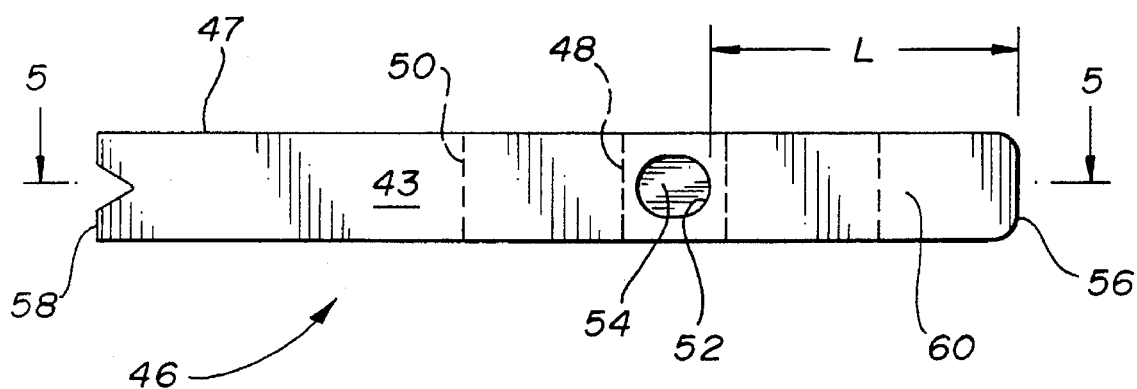
FIG. 4 is a planar view of a strip employed with the apparatus of this invention.
Figure 5:
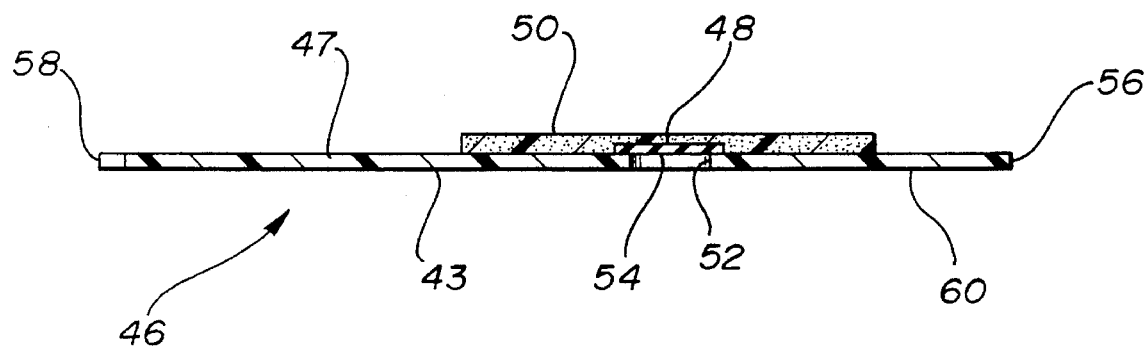
FIG. 5 is a longitudinal cross-sectional view of the strip of FIG. 4, taken along 5—5 of FIG. 4.

Referring now to FIGS. 4 and 5, FIG. 4 illustrates a planar view of the bottom surface 43 of a strip 46 embodying the teachings of this invention. FIG. 5 is a longitudinal, cross-sectional view of strip 46, taken through line 5—5 of FIG. 4. In the embodiment for detecting glucose in whole blood, the strip 46 comprises an elongate and generally rectangular support 47 onto which is attached a test pad 48 containing reactants and provided with an overlying transport medium 50. In use, the sample is to be applied to the top surface of the transport medium 50 overlying the test pad 48. A portion of the sample penetrates through the test pad and any glucose present reacts with the reactants therein to produce a color change which is visible on the bottom surface of the test pad. A support aperture 52 is provided through the support for aligning with aperture 30 in the lower guide of the apparatus when the strip is fully inserted therein, so that a portion of the bottom of the surface of the test pad will be visible to the optics of the apparatus (such portion hereinafter the reaction zone 54).

Details of these components of the strip are described in copending U.S. Ser. No. 881,970, filed May 12, 1992 and incorporated herein by reference. Briefly, the transport medium 50 comprises pores which drain the sample therethrough by capillary action. The transport medium may be composed of natural materials such as cotton or paper, as well as such synthetic materials as polyesters, polyamides, polyethylene and the like.

The transport medium has pores having an effective diameter in the range of about 20 microns to about 350 microns, preferably about 50 to about 150 microns, e.g., 100 microns. The transport medium is generally hydrophilic or may be rendered hydrophilic by treatment with surfactants compatible with red blood cells. One such compatible surfactant is MAPHOS™ 66 sold by Mazer Chemical, a division of PPG Industries Inc. Chemicals of Gurnee, Ill. In a preferred embodiment, the transport medium is capable of absorbing blood samples of up to about 20 to about 40 microliters, e.g, 30 microliters.

The transport medium may be, for example, a filter paper or sintered plastic material, such as those porous polyethylene materials commonly available from the Porex Corp. of Fairburn, Ga. The transport medium is generally fabricated to have a thickness of about 0.022 inch, with about 0.25 inch width and about 1.0 inch length. The transport medium is treated with a red blood cell compatible surfactant solution. Since only about 3 to about 5 microliters of blood are required to saturate the testing pad, the transport medium will preferably possess a small void volume in order not to require large volumes of blood. Excess blood applied to the reagent strip is absorbed and held in the portion of the transport medium which extends beyond the test pad.

The transport medium 50 is attached to the test pad 48 by a sustained adhesive, such as, for example, acrylic or rubber based adhesives. However, hot melt adhesives are preferred. The adhesive may be placed in continuous strips located only near the perimeter of the test pad, leaving a central portion of the receiving surface of the test pad substantially unobstructed.

The test pad and its preparation are also set forth in detail in U.S. Pat. 4,935,346 and need not be described in detail herein. Essentially, the test pad is a hydrophilic porous matrix to which reagents may be covalently or non-covalently bound. Examples of a suitable material include polyamides, which are conveniently condensation polymers of monomers from 4 to 8 carbon atoms, where the monomers are lactams or combinations of diamines and dicarboxylic acids, polysulfones, polyesters, polyethylene, and cellulose based membranes. Other polymeric compositions may also be used. Further, the polymer compositions may be modified to introduce other functional groups so as to provide for charged structures, so that the surfaces may be neutral, positive, or negative, as well as neutral, basic, or acidic. The material of choice is a hydrophilic, anisotropic polysulfone membrane having pores varying in size from large to small through the thickness of the matrix. The preferred matrix is obtained from the Memtec America Corporation of Maryland and has an average pore size ranging from 0.34 to 0.4 micrometers e.g., 0.37 and a thickness of from about 125 to about 140 micrometers e.g., 130 micrometers. The ratio of the average diameter of the large to the small pores is about 100.

The transport medium is adapted to accept a whole blood sample and transport a detectable portion of the sample to the receiving surface by capillary action. The transport medium preferably extends past one or more ends of the test pad so as to form a reservoir for holding excess amounts of blood sample which may be present during actual use. It is usually more desirable to retain such excess amounts of the blood sample in the transport medium, rather than allowing the excess to drip upon the user or upon the viewing means in an uncontrolled fashion. Accordingly, it is preferred that the transport medium be capable of holding from about 20 to about 40 microliters of blood, preferably about 30 microliters of blood and of passing from about 3 to about 5 microliters of blood to the test pad.

The test pad is impregnated with a color forming reagent system specific to an analyte. Typical analytes are glucose, cholesterol, urea, and many others which will readily occur to those skilled in the art. Preferably, the color forming reagent system includes an enzyme which selectively catalyzes a primary reaction with the analyte of interest. A product of the primary reaction may be a dye which undergoes a change in color that is detectable at the reaction zone. Alternatively, the product of the primary reaction may be an intermediate which undergoes another reaction, preferably also enzyme catalyzed, and participates in a secondary reaction which, directly or indirectly, causes a dye to undergo a change in color which is detectable at the reaction zone.

An exemplary color-forming reagent system is the system which is specific to glucose and contains glucose oxidase, a peroxidase, and an oxidizable dye. Glucose oxidase is an enzyme, usually obtained from an Aspergillus Niger or Penicillium, that reacts with glucose and oxygen to produce gluconolactone and hydrogen peroxide. The hydrogen peroxide so produced, catalyzed by a peroxidase enzyme, such as horseradish peroxidase, oxidizes a dye. The resulting chromohore (the oxidized dye) exhibits a color that may be observed at the reaction zone. Many suitable oxidizable dyes are known in the art including, for example, those set out in the aforementioned refereed U.S. Pat. No. 5,304,468. One particularly useful oxidizable dye is the 3-methyl-2-benzothiazolinone hydrazone hydrochloride/8-anilino 1-napthalenesulfonate dye couple (MBTH/ANS couple) described in copending U.S. patent application Ser. No. 245,940, filed May 19, 1994 (LFS-30). Many other suitable color-forming reagent systems specific to particular analytes are known in the art. A dye couple of choice is a derivative of MBTH, meta[3-methyl 2-benzothiazolinone hydrazone] N-sulfonyl benzenesulfonate, monosodium coupled with ANS. This combination is described in detail in U.S. patent application Ser. No. 08/302,575 filed today and incorporated herein by reference.

The support 46 may be of a material that is sufficiently rigid to be inserted into the apparatus without undue bending or kinking. Preferably, such support comprises material such as polyolefins (e.g., polyethylene or polypropylene), polystyrene or polyesters. A preferred material is the polyester available from the Imperial Chemical Industries, Ltd. of the United Kingdom and sold by them under the tradename Melinex 329 and having a thickness of about 0.014 inches.

In viewing FIG. 4, the bottom surface of the strip (i.e., the surface to be inserted in face-to-face relationship with the aperture 30 of the lower guide of the apparatus and, hence, the surface "seen" by the optics of the apparatus), it can be seen that this surface presents a reaction zone 54 comprised of the portion of the test pad 48 visible through the support aperture 52. The reaction zone 54 is longitudinally placed between the leading edge 56 of the strip (leading with respect to insertion into the apparatus) and the opposite edge 58.

Figure 7A:
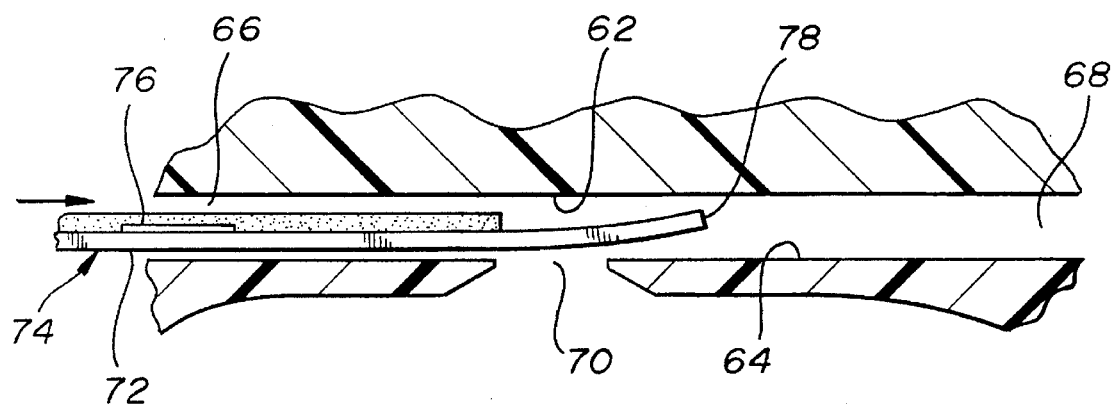
FIG. 7a is a schematic, fragmented, longitudinal cross-sectional view of a passageway as a strip is being inserted therein.
Figure 7B:
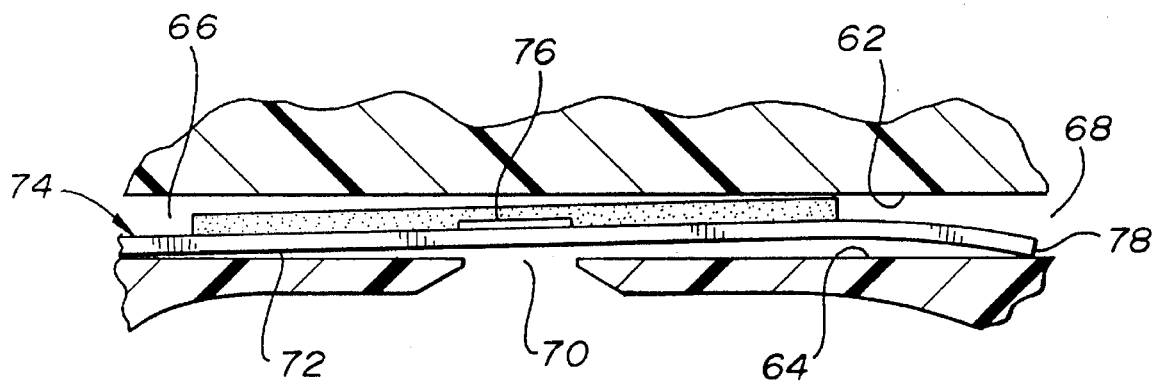
FIG. 7b is a schematic, fragmented, longitudinal cross-sectional view of the passageway of FIG. 7a with the strip now fully inserted.

The advantages of this invention will be best understood by consideration of FIGS. 7a–9. In FIGS. 7a and 7b, illustrated therein in schematic, longitudinal cross-section, are views of a strip passageway which does not incorporate the teachings of this invention but instead comprises a passageway 60 defined by upper wall 62 and lower wall 64 and having an open end 66 and an opposed end 68. Lower wall 64 is provided with an aperture 70 through which portions of the bottom surface 72 of the strip 74 are to be viewed by optics (not shown). Strip 74 is provided with a test pad 76 and hence, has a somewhat non-uniform planar top surface and is of a non-uniform thickness; i.e., it is generally thicker at the test pad portion than at the leading edge 78, for example. Accordingly, the walls 62 and 64 must be spaced apart to a sufficient degree to permit the thickest part of the strip to pass easily into the passageway 60. Concomitantly, the thinner leading edge 78 will have substantial "play" within the passageway. Accordingly, any degree of curl or non-planar configuration of the leading edge of the strip will cause the bottom surface of this portion to vary in distance from the aperture 70 as the strip is inserted into the passageway. This lack of maintaining a precise presentation to the aperture will result in an erroneous reading by the optics of the apparatus. FIG. 7a shows this curl as being toward the upper wall 62, whereas FIG. 7b shows the curl to be toward the bottom wall 64. It will be appreciated that while a strip of varying thickness aggravates the above-described problem, even if the strip were of uniform thickness, some clearance must be provided and, hence, albeit to a less extent, the problem will still exist. Moreover, while the problem has been described in terms of the strip being nonplanar, i.e., curled in the longitudinal direction, it will be understood that a similar situation arises when the strip is nonplanar transversely; e.g., twisted.

FIG. 8 illustrates a strip passageway 80 adhering to the teachings of this invention. Again, passageway 80 is defined by lower first wall 84 and an upper second wall 82 with an aperture 90 provided through the first wall 84. The passageway is designed to accommodate a strip 94, having a bottom surface 92 and a test pad 96 and, hence, similar to the strip shown in FIGS. 7a and 7b. In accordance with the teachings of this invention, however, the first wall 84 is provided with a first strip bearing surface 85 and the second wall 82 is provided with a second strip bearing surface 87 downstream of the first strip bearing surface 85 with both such strip bearing surfaces 85, 87 being located upstream of the aperture 90. The bearing surfaces 85 and 87 are further oriented with respect to each other so that the portion of the strip 89 overlying the aperture 90 is urged against the aperture 90. This is accomplished by providing the bearing surfaces 85 and 87 in an orientation which forces the strip into a curved shape concave to the second wall 82 and by providing a strip 94 having spring-like properties. The spring-like strip 94, forced into such curved shaped will be biased to straighten and hence be urged against the aperture 90. To accomplish this curvature the two bearing surfaces should be oriented so that the upstream first bearing surface 85 is at a sufficient height above the plane of the aperture relative to the height of the second bearing surface 87. If the first bearing surface is positioned much below the second bearing surface, the strip introduced into the passageway will not be forced into the desired curvature. Accordingly, the first bearing surface must be no lower than one strip thickness below the second bearing surface 87. As illustrated by the dashed tangent lines to the surfaces in FIG. 8, bearing surface 85 is preferably higher than the bearing surface 87 and hence it is assured that the strip 94 will be forced into the desired curvature.

The strip 94 illustrated in FIG. 8 is shown as having at least two different thicknesses, i.e., thickest at the test pad 87 and thinner upstream and downstream of the test pad. The relative height of the two bearing surfaces prescribed above should be determined in this case by the thinnest portion of the strip passing between the two bearing surfaces when an upstream portion of the strip, whose surface is to be read by the optics of the apparatus, overlies the aperture. On the other hand, the distance between the two bearing surfaces, as projected on a plane parallel to the plane of the aperture, is then determined by the maximum thickness of the strip and should be such that the thickest part of the strip can be readily inserted into the passageway between the bearing surfaces.

As illustrated in FIG. 8, when the strip 94 is inserted by imposing a force shown by the vector arrow F, the shape of the walls force the strip into a curved configuration. Because the apparatus is adapted to be used in conjunction with a strip having spring-like properties, the curved strip will attempt to straighten. This attempt to straighten translates as a force shown by the vector arrow S, which biases the leading portion 89 of the strip against the aperture. By virtue of this arrangement, any time a portion of the strip overlies the aperture, such portion will be biased against the aperture and, hence, be uniformly presented to the optics of the apparatus.

The spring-like characteristics of the strip need be of a degree only sufficient to manifest the downward force as the strip is inserted. Strips constructed of 14 mil Melinex 329 polyester as obtained from Imperial Chemical Industries Ltd., or a 20 mil high impact polystyrene as obtained from the Spartech Company, have the requisite springiness. Employing a CHATILLION Tester, spring constants have been determined for these materials by having such strip span two supports with the spanning distance being one-half inch. A force applied at the center of the span to create a strain rate of 1 inch per minute is imposed and a stress-stained curve is generated. The slope of the linear portion of such curve is taken as the spring constant and is found to vary from about 12 to about 22 pounds force/inch. It is believed that strips with spring constants as low as 7 lbs. force/inch will be suitable for use in connection with this invention, although preferably such constants should be at least 10 lbs. force/inch. Such constants may be as high as 40 lbs. force/inch and preferably less than 30 lbs. force/inch.

A still more preferred configuration is illustrated in FIG. 9 wherein the strip 94 of FIG. 8 is illustrated as completely inserted into the passageway (like parts in FIGS. 8 and 9 carry like part numbers). In this case, however, the upper wall 82 is further provided with a third bearing surface 97 positioned downstream of aperture 90. Preferably this third bearing surface 97 is oriented to be no higher than one strip thickness above the plane of the aperture. Accordingly, the leading portion of the strip 89 having reached the position downstream of the aperture will bear against this third bearing surface 97 and deflect into a curved shape concave to the first wall 84. This deflection will maintain the portion of the strip overlying the aperture firmly against the aperture.

Figure 6:
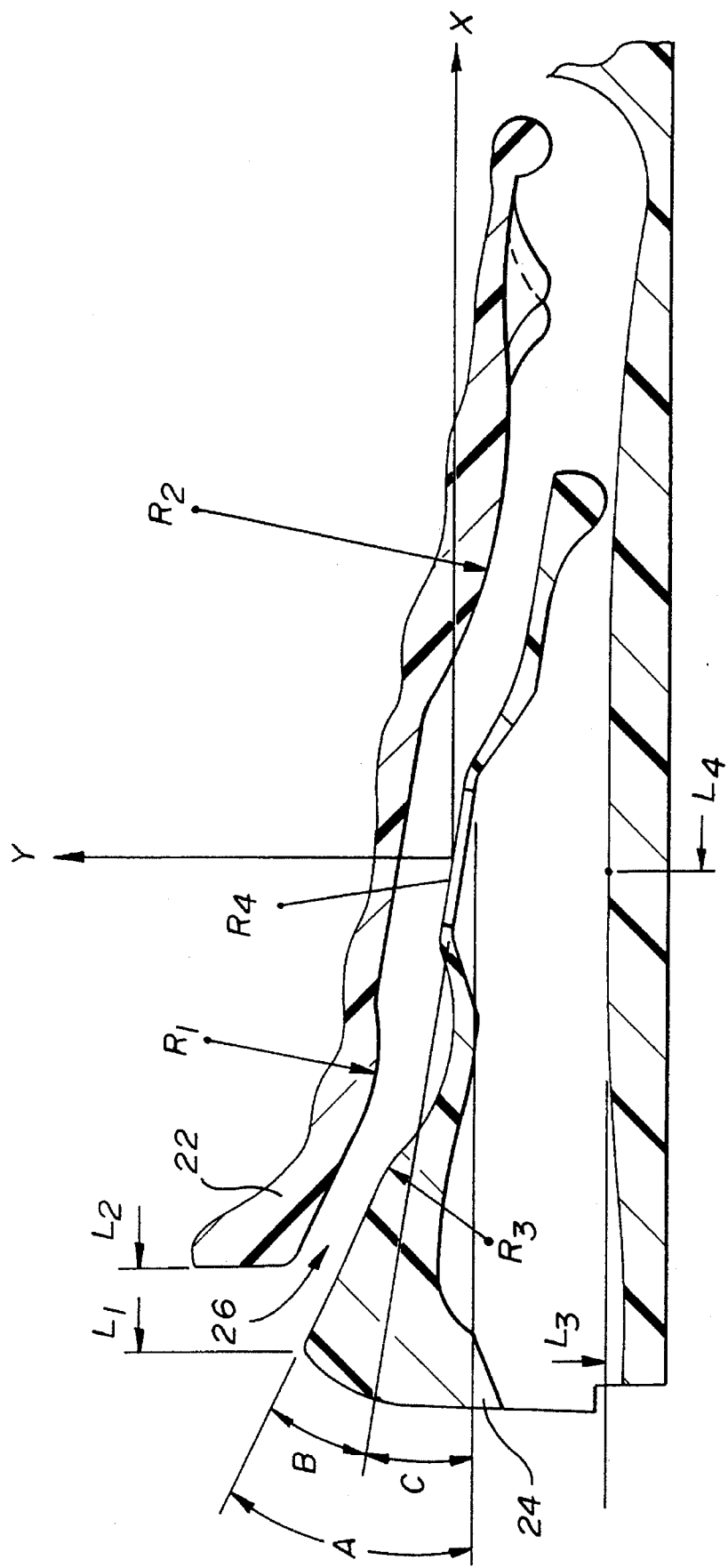
FIG. 6 is a longitudinal, cross-sectional view of the strip passageway in an apparatus embodying this invention.

It will be appreciated by those skilled in the art, that the drawings shown in FIGS. 7, 8 and 9 are schematic and, especially for FIGS. 8 and 9, greatly exaggerate the deviations of the curved walls from straight walls. FIG. 6 is more typical of upper guide 22 and lower guide 24 which carry upper wall 23 and lower wall 25, respectively.

Table 1 below recites preferred dimensions for the angles, distances and radii; all based on the X,Y coordinates shown in FIG. 6.

TABLE 1

DIMENSIONS FOR FIG. 6

| ANGLES (Degrees) | |
|---|---|
| A | 26 |
| B | 17 |
| C | 9 |

| DISTANCES (Inches) | |
|---|---|
| $L_1$ | 0.562 |
| $L_2$ | 0.467 |
| $L_3$ | 0.184 |
| $L_4$ | 0.013 |

| CURVATURE | | |
|---|---|---|
| | RADIUS (Inches) | CENTER (X,Y In) |
| $R_1$ | 0.2 | 0.207, 0.179 |
| $R_2$ | 0.347 | 0.391, 0.300 |
| $R_3$ | 0.100 | 0.417, 0.006 |
| $R_4$ | 2.635 | 0.412, 2.603 |

The invention having now been fully described, it will be apparent to one skilled in the art that any modifications and changes may be made thereto without departing from the spirit and scope of the invention as is defined in the following claims.

What is claimed is:

1. An apparatus for measuring an analyte in a sample applied to a portion of a longitudinally extending strip inserted into said apparatus by reading a reflectance at at least one reading position on the strip, wherein said strip has a leading edge and a trailing edge with respect to insertion into said apparatus, the apparatus comprising:

a strip passageway defined by first and second walls extending longitudinally from an upstream open end for accepting said leading edge of said strip to a downstream opposed end;

an aperture in said first wall for rendering a portion of an inserted strip visible through said aperture;

said first wall having a first strip bearing surface and said second wall having second and third strip bearing a downstream from said first bearing surface, said second bearing surface being upstream of said aperture and said third bearing surface being downstream of said aperture, said surfaces being oriented to urge a portion of an inserted strip downstream of the second strip bearing surface against said aperture when said at least one reading position overlies said aperture.

2. The apparatus of claim 1 wherein said bearing surfaces are oriented to urge the inserted strip into a curved shape concave to the second wall.

3. The apparatus of claim 2 wherein the upstream first bearing surface is no lower than one strip thickness below the downstream second bearing surface when the strip is therebetween and positioned to be read through the aperture.

4. The apparatus of claim 3 wherein the upstream first strip bearing surface is above the downstream second strip bearing surface.

5. The apparatus of claim 1 wherein said third bearing surface is oriented to deflect the strip into a curved shape concave to the first wall.

6. The apparatus of claim 5 wherein said third bearing surface is oriented no higher than one strip thickness above the aperture.

* * * * *

UNITED STATES PATENT AND TRADEMARK OFFICE
CERTIFICATE OF CORRECTION

PATENT NO. : 5,515,170
DATED : May 7, 1996
INVENTOR(S) : Matzinger, David P. and Daffern, George M.

It is certified that error appears in the above-indentified patent and that said Letters Patent is hereby corrected as shown below:

Col. 12, line 42, after "bearing" replace "a" with "surfaces"

Signed and Sealed this

Thirtieth Day of July, 1996

Attest:

BRUCE LEHMAN

*Attesting Officer*  *Commissioner of Patents and Trademarks*